US006277385B1

(12) United States Patent
Luke

(10) Patent No.: US 6,277,385 B1
(45) Date of Patent: Aug. 21, 2001

(54) COOLING COMPOSITIONS WITH REDUCED STINGING

(75) Inventor: William Michael Luke, Blue Ash, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 08/375,193

(22) Filed: Jan. 18, 1995

Related U.S. Application Data

(63) Continuation of application No. 08/185,104, filed on Jan. 21, 1994, now abandoned, which is a continuation of application No. 07/900,219, filed on Jun. 17, 1992, now abandoned.

(51) Int. Cl.[7] .................. A61K 7/40; A61K 7/48
(52) U.S. Cl. .................. 424/401; 424/70.1; 424/73; 424/59; 514/859; 514/887
(58) Field of Search .......... 424/401, 59, 195.1, 424/70.1, 73; 512/12, 22; 524/859, 887

(56) References Cited

U.S. PATENT DOCUMENTS

| | | | | |
|---|---|---|---|---|
| 3,936,398 | * | 2/1976 | Tavares et al. | 512/12 |
| 4,136,163 | * | 1/1979 | Watson et al. | 424/73 |
| 4,136,164 | | 1/1979 | Rowsell et al. | 424/54 |
| 4,137,304 | | 1/1979 | Rowsell et al. | 424/54 |
| 4,137,305 | | 1/1979 | Rowsell et al. | 424/54 |
| 4,153,679 | * | 5/1979 | Rowsell et al. | 424/73 |
| 4,230,688 | * | 10/1980 | Rowsell et al. | 424/73 |
| 4,248,859 | | 2/1981 | Rowsell et al. | 424/54 |
| 4,279,891 | | 7/1981 | Henkel et al. | 424/73 |
| 4,296,255 | | 10/1981 | Rowsell et al. | 564/215 |
| 4,548,743 | * | 10/1985 | Sprecker | 512/22 |
| 4,758,599 | | 7/1988 | Minetti | 514/844 |
| 5,009,893 | | 4/1991 | Cherukuri et al. | 424/440 |

FOREIGN PATENT DOCUMENTS

| | | |
|---|---|---|
| 2608-226 | 9/1977 | (DE) . |
| 0 507 190 A1 | 10/1992 | (EP) . |
| 1315626 | 5/1973 | (GB) . |
| 1351761 | 5/1974 | (GB) . |
| 1404596 | 9/1975 | (GB) . |
| 1422998 | 1/1976 | (GB) . |
| 1432354 | 4/1976 | (GB) . |
| 1434728 | 5/1976 | (GB) . |
| 138085 | 4/1982 | (JP) . |

OTHER PUBLICATIONS

Watson, Hems, Rowsell, and Spring, "New Compounds With The Menthol Cooling Effect", J. Soc. Cosmet. Chem., vol 29, No. 4, pp 185–200, Apr. 1978.

* cited by examiner

Primary Examiner—Thurman K. Page
(74) Attorney, Agent, or Firm—Leonard W. Lewis; William J. Winter

(57) ABSTRACT

The present invention provides coolant compositions for topical application to the skin which can provide long-lasting cooling with low or reduced skin sting. The compositions comprise a mixture of specific type of acyclic carboxamide coolant with a specific type of 3-substituted-p-menthane coolant, an aqueous vehicle, and no more than about 30% $C_1$–$C_6$ monohydric alcohol.

21 Claims, No Drawings

COOLING COMPOSITIONS WITH REDUCED STINGING

This is a continuation of application Ser. No. 08/185,104, filed on Jan. 21, 1994 now abandoned, which was a continuation of application Ser. No. 07/900,219, filed on Jun. 17, 1992 now abandoned.

TECHNICAL FIELD

This invention relates to low-stinging coolant compositions for application to the skin characterized by containing a multiplicity of specific coolant compounds and low or zero levels of alcohol solvents.

BACKGROUND

Compositions of various types have incorporated within them components which provide cooling sensation to skin. Such compositions include perfumes, lotions, shaving cream and gels, post-shaving preparations, shampoos, antiperspirants, deodorants, anti-acne medicines, first aid ointments, and a variety of other skin care and pharmaceutical products that are applied to the skin.

It is well established that the "cooling" effect of menthol is a physiological effect due to the direct action of menthol on the nerve endings of the human body responsive for the detection of hot or cold and is not due to latent heat of evaporation. It is believed that the menthol acts as a direct stimulus on the cold receptors at the nerve endings which in turn stimulate the central nervous system.

Although menthol is well established as a physiological coolant, its use and effectiveness is limited in some types of compositions by its strong minty odor and its relative volatility, particularly for perfumes, colognes, pre- or post-shave lotions, etc., where aroma is an important aesthetic attribute. The high volatility of menthol limits the period of time which it can provide cooling sensation. The high volatility of menthol can also result in eye sting for compositions applied to the face or in the vicinity of the eyes.

The cooling effect of menthol and other related terpene alcohols and their derivatives has also been studied and reported in Koryo, 95, (1970), pp. 39–43. 2,3-p-menthane diol has also been reported as having a sharp cooling taste (Beilstein, Handbuch der Organischen Cheme, 4th Ed. (1923) Vol. 6, p. 744).

Carboxamides have also been disclosed for use as coolants in a variety of compositions. Two patents describing such materials and compositions are U.S. Pat. No. 4,136,163, Jan. 23, 1979 to Watson et al. and U.S. Pat. No. 4,230,688, Oct. 28, 1980 to Rowsell et al. These patents as well as those set forth above are incorporated herein in their entirety by reference.

Ethanol and other volatile alcohols are commonly used in topical skin compositions to provide a coolant effect. The cooling sensation from volatile alcohols is due primarily to the latent heat of evaporation from the skin. After shave and pre-shave lotions typically contain high levels of ethanol, since it provides a cooling effect and does not interfere with the pleasing aroma typically associated with these products. Ethanol provides a strong initial cooling sensation, however cooling dissipates relatively rapidly as the ethanol evaporates. Unfortunately, the volatile alcohols also tend to impart a stinging sensation in addition to cooling, particularly with respect to skin that has been cut or recently shaved.

It is an object of this invention to provide improved coolant compositions for topical application to the skin.

In particular, it is an object of this invention to provide coolant compositions for application to the skin which can provide an improved cooling in combination with low sting to the skin and eyes.

It is a further object of this invention to provide coolant compositions, as described above, which can provide improved cooling over an extended period of time.

It is yet another object of this invention to provide such improved coolant compositions which need not contain aromatic ingredients, such as menthol, which can cause eye sting or adversely interfere with other fragrances incorporated into the composition.

The invention hereof, including its essential elements as well as a variety of additional ingredients, is described below. The compositions and method hereof can comprise, consist of, or consist essentially of the essential elements as well as any of the additional ingredients or limitations discussed herein.

All percentages reported herein are by weight of the total composition and all ratios are by weight unless otherwise specifically indicated.

SUMMARY OF THE INVENTION

The present invention provides aqueous coolant compositions useful for topical application to the skin which impart minimal or no sting and are characterized by both good initial cooling and long lasting cooling sensation upon application to the skin, without requiring the use of odoriferous coolants. The compositions hereof are particularly suitable for pre- and post-shave lotions, perfumes, colognes, etc.

The compositions hereof comprise mixture of particular coolants in an aqueous carrier which contains no more than about 30%, by weight, $C_1$–$C_6$ alcohol.

The present invention also provides a method for providing a cooling sensation to the skin comprising applying an effective amount of a composition hereof to the skin.

More specifically, the compositions of the present invention comprise:

(I) a first coolant component which is an acyclic carboxamide coolant component of the formula:

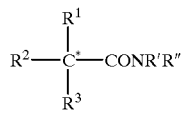

where:
(i) R' and R" independently are hydrogen, $C_1$–$C_5$ alkyl, or $C_1$–$C_8$ hydroxyalkyl, R' and R" provide a total of no more than 8 carbon atoms, and when R' is hydrogen, R" may also be alkyl-carboxyalkyl of up to 6 carbon atoms
(ii) R' and R", when taken together, represent an alkylene group of up to 6 carbon atoms, the opposite ends of which are attached to the amide nitrogen atom to form a nitrogen heterocycle, the carbon chain of which optionally being interrupted by oxygen;
(iii) $R^1$ is hydrogen or $C_1$–$C_5$ alkyl; $R^2$ and $R^3$ independently are $C_1$–$C_5$ alkyl; with the proviso that: (a) $R^1$, $R^2$, and $R^3$ together provide a total of at least 5 carbon atoms; and (b) when $R^1$ is hydrogen, $R^2$ is $C_2$–$C_5$ alkyl and $R^3$ is $C_3$–$C_5$ alkyl and at least one of $R^2$ and $R^3$ is branched;

(II) a second coolant component which is a 3-substituted-p-menthane of the formula:

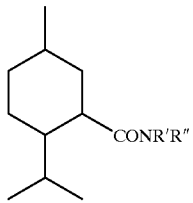

where
R' is hydrogen or an aliphatic radical containing up to 25 carbon atoms;
R" is hydroxy or an aliphatic radical containing up to 25 carbon atoms, with the proviso that when R' is hydrogen R" may also be an aryl radical of up to 10 carbon atoms selected from the group consisting of substituted phenyl, phenalkyl and substituted naphthyl, and pyridyl; and R' and R", when taken together with the nitrogen atom to which they are attached, represent a cyclic or heterocyclic group of up to 25 carbon atoms;

(III) an aqueous vehicle suitable for topical application to the skin; and (IV) a cosmetically active ingredient or medicament; wherein said composition contains no more than about 30% by weight of $C_1$–$C_6$ monohydric alcohol.

In other embodiments hereof, the compositions contain other cosmetic ingredients or medicaments suitable for application to the skin in place of or in addition to fragrance.

DETAILED DESCRIPTION OF THE INVENTION

The essential as well as various optional elements of the compositions of the invention are described below. In general, the compositions contain a mixture of particular carboxamide coolants, water, and no more than about 30%, by weight, of $C_1$–$C_6$ monohydric alcohols. The compositions hereof also contain a perfume or other cosmetic ingredient or medicament suitable for application to the skin, or a mixture thereof.

First Coolant Component

The compositions hereof contain as an essential component certain acyclic tertiary and/or secondary carboxamides of the following formula:

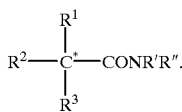   I where R' and R", when taken separately, are each hydrogen, $C_1$–$C_5$ alkyl or $C_1$–$C_8$ hydroxyalkyl and provide a total of no more than 8 carbon atoms, with the proviso that when R' is hydrogen R" may also be alkylcarboxyalkyl of up to 6 carbon atoms;

R' and R", when taken together, represent an alkylene group of up to 6 carbon atoms, the opposite ends of which group are attached to the amide nitrogen atom thereby to form a nitrogen heterocycle, the carbon chain of which may optionally be interrupted by oxygen;

$R^1$ is hydrogen or $C_1$–$C_5$ alkyl; and $R^2$ and $R^3$ are each $C_1$–$C_5$ alkyl; with the provisos that (i) $R^1$, $R^2$ and $R^3$ together provide a total of at least 5 carbon atoms, preferably from 5–10 carbon atoms; and (ii) when $R^1$ is hydrogen, $R^2$ is $C_2$–$C_5$ alkyl and $R^3$ is $C_3$–$C_5$ alkyl and at least one of $R^2$ and $R^3$ is branched, preferably in an alpha or beta position relative to the carbon atom marked (*) in the formula.

The preferred amides used in this invention are the tertiary compounds, i.e., those where each of $R^1$, $R^2$ and $R^3$ is $C_1$–$C_5$ alkyl, especially those where $R^1$ is methyl, ethyl or n-propyl and at least one of $R^2$ and $R^3$ is a branched chain group having branching in an alpha or beta position relative to the C atom marked (*) in the formula. Also preferred are non-substituted amides, i.e., where R' is H, and disubstituted amides where R' and R" are methyl or ethyl. A further preferred group consist of amides of the formula given where $R^1$ is hydrogen and at least one of $R^2$ and $R^3$ is branched in an alpha position relative to the carbon atom marked * in the formula.

Other preferred coolants within the scope of the above formula are monosubstituted tertiary amides of the formula:

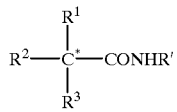   I(a)

where $R^1$, $R^2$ and $R^3$ are each $C_1$–$C_5$ alkyl and together provide a total of at least 5, preferably 5–10 carbon atoms; and R' is $C_1$–$C_5$ alkyl, $C_1$–$C_8$ hydroxyalkyl or alkylcarboxyalkyl of up to 8 carbon atoms. In this group $R^1$ is preferably methyl, ethyl or n-propyl and one or both of $R^2$ and $R^3$ is branched in an alpha or beta position relative to the carbon atom marked (*).

Coolants of the above description are also described in U.S. Pat. No. 4,230,688, Rowsell et al., issued Oct. 28, 1990 (Wilkinson Sword Limited, England), which is incorporated herein by reference.

Second Coolant Component

The compositions hereof contain as a second essential coolant component an N-substituted-p-menthane-3-carboxamide, or a particular type of ketal as will be described below, or a combination thereof.

The N-substituted-p-menthane-3-carboxamides are 3-substituted-p-menthanes of the formula:

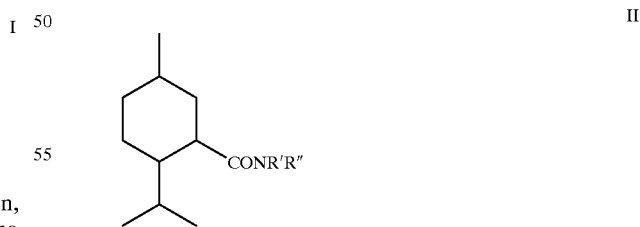   II where R', when taken separately, is hydrogen or an aliphatic radical containing up to 25 carbon atoms; R" when taken separately is hydroxy, or an aliphatic radical containing up to 25 carbon atoms, with the proviso that when R' is hydrogen R" may also be an aryl radical of up to 10 carbon atoms and selected from the group consisting of substituted phenyl, phenalkyl or substituted phen-alkyl, naphthyl and substituted naphthyl, pyridyl; and R' and R", when taken together with the nitrogen atom to which they are attached, represent a cyclic or heterocyclic group of up to 25 carbon atoms, e.g. piperidino, morpholino etc.

In the above definitions "aliphatic" is intended to include any straight-chained, branched-chained or cyclic radical free or aromatic unsaturation, and thus embraces alkyl, cycloalkyl, alkenyl, cycloalkenyl, alkynyl, hydroxyalkyl, acyloxyalkyl, alkoxy, alkoxyalkyl, aminoalkyl, acylaminoalkyl, carboxyalkyl and similar combinations.

Typical values for R' and R" when aliphatic are methyl, ethyl, propyl, butyl, isobutyl, n-decyl, cyclopropyl, cyclohexyl, cyclopentyl, cycloheptylmethyl, 2-hydroxyethyl, 3-hydroxy-n-propyl, 6-hydroxy-n-hexyl, 2-aminoethyl, 2-acetoxyethyl, 2-ethyl-carboxyethyl, 4-hydroxybut-2-ynyl, carboxymethyl etc.

When R" is aryl typical values are benzyl, naphthyl, 4-methoxyphenyl, 4-hydroxyphenyl, 4-methylphenyl, 3-hydroxy-4-methylphenyl, 4-fluorophenyl, 4-nitrophenyl, 2-hydroxynaphthyl, pyridyl, etc.

Substitution of the amide group in the 3-position of the p-menthane structure also gives rise to optical isomerism, existing in d, 1 and d1 forms. The physiological cooling effect is believed to generally be greater in the 1-form than in d-form.

When either R' and R" is aliphatic the preferred values are $C_1$–$C_9$ straight or branched chain alkyl, $C_1$–$C_9$ straight or branched chain hydroxyalkyl or aminoalkyl and $C_1$–$C_4$ acylated derivatives thereof, and —$C_nH_{2n}COR'''$ or —$C_nH_{2n}COOR'''$, where —$C_nH_{2n}$ is a straight or branched chain alkylene radical in which n is an integer of from 1–6 and R''' is hydrogen or a $C_1$–$C_8$ alkyl or hydroxyalkyl group, preferably a $C_1$–$C_4$ straight chain alkyl group.

More preferred are monosubstituted compounds, i.e., where R' is H. Also preferred are di-substituted compounds where R' and R" are both $C_1$–$C_3$ alkyl which also show a very pronounced cooling effect. Most preferred of all are compounds where R' is H and R" is $C_1$–$C_3$ alkyl, $C_1$–$C_4$ hydroxyalkyl, or —$CH_2COOR'''$, where R''' is $C_1$–$C_4$ alkyl.

Also included within the scope of this invention are compounds where R' is H and R" is hydroxy or substituted phenyl, e.g., alkylphenyl, hydroxyphenyl, alkoxyphenyl, halophenyl of up to 10 carbon atoms, phenalkyl or substituted phenalkyl e.g., benzyl, naphthyl or substituted naphthyl, and compounds where R' and R" are joined to form a cyclic group. When so joined R' and R" preferably represent an alkylene chain, optionally interrupted by oxygen, which together with the nitrogen atom to which R' and R" are attached forms a 5- or 6-membered heterocyclic ring.

Compounds of the type described above are described in U.S. Pat. No. 4,136,163, Watson et al., issued Jan. 23, 1979 (Wilkinson Sword Limited, England), which is incorporated herein by reference.

Optionally, other coolant ingredients can be included in the compositions hereof to benefit from the particular characteristics of such coolants. Any coolant ingredient suitable for topical applicaton to skin can be used. One type which is particularly preferred includes ketal coolant compounds the formula:

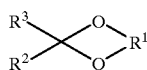

III in which $R^1$ represents a $C_2$–$C_6$-alkylene radical having at least 1, but not more than 3, hydroxyl group(s), preferably 1 hydroxyl group, and either $R^2$ and $R^3$ independently of one another represent $C_1$–$C_{10}$-alkyl which is optionally substituted by 1 to 3 radicals selected from the group comprising hydroxyl, amino and halogen (such as fluorine, chlorine, bromine or iodine), $C_5$–$C_7$-cycloalkyl, preferably cyclohexyl, $C_6$–$C_{12}$-aryl, preferably phenyl, with the proviso that the total of the carbon atoms of $R^2$ and $R^3$ is not less than 3, or $R^2$ and $R^3$ together represent an alkylene radical which, together with the carbon atom which carries the radicals $R^2$ and $R^3$, forms a 5–7-membered ring, it being possible for this alkylene radical, in turn, to be substituted by $C_1$–$C_6$-alkyl groups.

Preferred radicals $R^2$ and $R^3$ comprise methyl, isopropyl and tert.-butyl.

The length of the radicals $R^2$ and $R^3$ influences the effect of the compounds: shorter radicals lead to an immediate, short effect; longer radicals lead to a delayed, but prolonged effect. An important aspect for the cosmetics industry is the solubility of the compounds in water; this is the case, in particular, with short radicals $R^2$ and $R^3$. However if prolonged cooling effect is desired, the water insoluble ketal coolants can be emulsified (including microemulsions) or otherwise dispersed in the compositions hereof through conventional techniques, such as with emulsion-forming surfactants, suspending agents, or solubilization in solvent which is then dispersed, emulsified, or suspended in the composition.

Preferred radicals $R^1$ embrace 1,2- and 1,3-alkylene radicals which, together with the two oxygen atoms and with the carbon atom to which the two oxygen atoms are attached, form a dioxolane or dioxane ring.

Preferred compounds III in which $R^2$ and $R^3$ together represent an alkylene radical are those of the formula

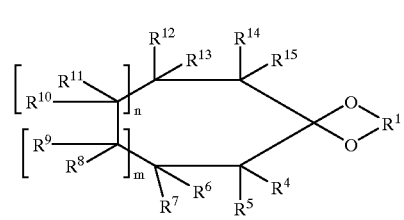

III(a)

in which $R^4$ to $R^{15}$ independently of one another denote hydrogen or $C_1$–$C_6$-alkyl, preferably hydrogen or $C_1$–$C_4$-alkyl, and m and n independently of one another denote zero or 1.

Preferred compounds of the formula III (a), are those in which the total of m+n is 1, i.e. ketals of an optionally substituted cyclohexanone.

Preferred substituents, of which there may be present, in particular, 1 to 3, are methyl, isopropyl and tert.-butyl.

The ketals III can be prepared by known processes. For example, ketal III will generally be prepared by acid-catalysed reaction of the ketone on which ketal III is based and not less than the equivalent amount of aliphatic $C_3$–$C_6$-alcohol having not less than 3 and not more than 5, preferably 3, hydroxyl groups. In general, the ketal will be made by reaction of the ketone on which ketal III is based and not less than 0.5 mol equivalents of the $C_3$–$C_6$-alcohol having 3 to 5 hydroxyl groups will be employed. Preferably, a 1.2- to 4-fold, preferably 1.5- to 3-fold excess of this amount of the alcohol is used. Examples of acid catalysts which can be used are p-toluenesulphonic acid, phosphoric acid or potassium hydrogen sulphate in catalytically effective amounts (for example 0.1 to 3 g of p-toluenesulphonic acid per mole of ketone). The reaction will preferably be carried out either in an organic solvent which together with water forms an azeotrope, so that the water, which is liberated during the formation of the ketal, can be eliminated by azeotropic entrainment, or water-consuming coreagents such as, for example, trialkyl ortho esters. Examples of preferred organic solvents comprise benzene, toluene, xylene, chloroform, methylene chloride and trichloroethylene.

The reaction can be regarded as complete when water no longer separates out or when an ester/alcohol mixture is no longer separated out. It is recommended to wash the products subsequently with dilute alkali and with water, to separate and dry the organic phase, to strip off the solvent and, if appropriate, to purify the residue, for example by distillation.

Particularly preferred ketals III are those of the formulae

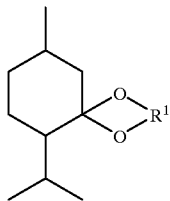

(IV)

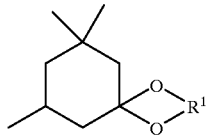

(V)

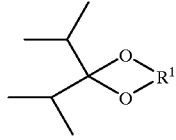

(VI)

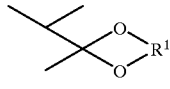

(VII)

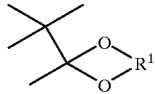

(VIII)

in which $R^1$ has the above-mentioned meaning, particularly preferred substances from among the ketals IV to VIII being in each case the glycerol ketals.

The ketals III can have asymmetric carbon atoms; optical isomerism can therefore occur. Depending on the starting material and the preparation methods used, they can exist in the form a mixtures of the optical isomers or in the form of pure isomers. The cooling effect of the isomers may differ, so that one or the other isomer may be preferred.

Aqueous Vehicle

The coolant compositions hereof, suitable for topical application to skin, will comprise coolant component I together with coolant component II in an aqueous carrier. Lower alkyl chain alcohols are common vehicle ingredients in skin care compositions. However these alcohols can cause excessive levels of a stinging or burning sensation to the skin, especially cut or irritated skin. Therefore, the compositions hereof will contain no more than about 30%, by weight, of $C_1$–$C_6$ monohydric alcohols, preferably no more than about 25%, more preferably no more than about 20%, even more preferably no more than about 10%, most preferably from 0% to about 5%. It is especially preferred to limit the presence of $C_1$–$C_4$ monohydric alcohols, such as methanol, ethanol, propanol, isopropanol, and butanol, according to the preferred above levels.

Despite the restrictions on the use of alcohol in the present invention, the compositions hereof can provide coolant benefits upon application to the skin characterized by a strong initial cooling sensation and long lasting cooling with little or no burning sensation to the skin.

The essential component of the aqueous vehicle is water. Water will generally be present at levels of at least about 50% by weight of the composition, preferably from about 75% to about 99.8%, more preferably from about 80% to about 97%.

The coolant components can be present at any level effective for providing coolant effect upon application to the skin. In general, the weight ratio of coolant component I to coolant component II is from about 5:1 to about 1:5, preferably from about 3:1 to about 1:3, more preferably from about 3:1 to about 1:1.

Coolants I and II are each typically used at levels of at least about 0.01%, by weight of the composition, preferably at least about 0.1%. The upper limit that can be used for purposes of this invention will depend upon the particular coolants being used, as excessively high levels can result in a burning sensation upon application to the skin. In general, however, it is preferred to use coolants I and II each at levels from about 0.1% to about 1%, by weight, more preferably from about 0.1% to about 0.5%.

Coolant III, the optional ketal coolant, is generally used at levels of from about 0.1% to about 1.5%, more preferably from about 0.1% to about 0.75%, by weight of the composition.

Perfume

The compositions hereof will generally contain a perfume to impart a desired aroma, or to mask odors that may be associated with other components of the compositions. Any perfume suitable for application to the skin can be used. A wide variety of perfumes are known to those skilled in the art and are commercially available. The particular perfume used is largely a matter of choice. However the perfume should be used at a level effective for providing a noticeable aroma to the composition, or for masking undesired aroma of the composition. Also, the perfume and whatever carriers accompany it should not impart excessive stinging to the skin, especially broken or irritated skin, at the levels added. In general, the compositions will comprise from about 0.1% to about 10% of a perfume component, preferably from about 0.1% to about 7%, more preferably from about 0.1% to about 3%. As used herein, perfume means aromatically active ingredients whereas perfume component includes the perfume and any accompanying perfume solvent.

Perfumes are made by those skilled in the art in a wide variety of fragrances and strengths. Typical perfumes are described in Arctander, *Perfume and Flavour Chemicals* (Aroma Chemicals), Vol. I and II (1969); and Arctander, *Perfume and Flavour Materials of Natural Origin* (1960).

The perfumes selected for use herein are chosen not only for their scent and strength, but also to meet aesthetic demands of the consumer.

As disclosed in U.S. Pat. No. 4,322,308, Hooper et al., issued Mar. 30, 1982, and U.S. Pat. No. 4,304,679, Hooper et al., issued Dec. 8, 1981, both incorporated herein by reference, perfume components generally include, but are not limited to, volatile phenolic substances (such as iso-amyl salicylate, benzyl salicylate, and thyme oil red); essence oils (such as geranium oil, patchouli oil, and petitgrain oil); citrus oils; extracts and resins (such as benzoin siam resinoid and opoponax resinoid); "synthetic" oils (such as Bergamot 37 and 430, Geranium 76 and Pomeransol 314); aldehydes and ketones (such as B-methyl naphthyl ketone, p-t-butyl-A-methyl hydrocinnamic aldehyde and p-t-amyl cyclohexanone); polycyclic compounds (such as Coumarin and B-naphthyl methyl ether); esters (such as diethyl phthalate, phenyl-ethyl phenylacetate, non-anolide-1:4). Perfumes also include esters and essential oils derived from floral materials and fruits, citrus oils, absolutes, aldehydes, resinoides, musk and other animal notes (e.g., natural isolates of civet, castoreum and musk), balsamic, etc. and alcohols (such as dimyrcetol, phenyl-ethyl alcohol and tetrahydromuguol). Examples of such components useful in perfumes herein include decyl aldehyde, undecyl aldehyde, undecylenic aldehyde, lauric aldehyde, amyl cinnamic aldehyde, ethyl methyl phenyl glycidate, methyl nonyl acetaldehyde, myristic aldehyde, nonalactone, nonyl aldehyde, octyl aldehyde, undecalactone, hexyl cinnamic aldehyde, benzaldehyde, vanillin, heliotropine, camphor para-hydroxy phenolbutanone, 6-acetyl 1,1,3,4,4,6 hexamethyl tetrahydronaphthalene, alpha-methyl ionone, gamma-methyl ionone, and amyl-cyclohexanone and mixtures of these components.

Perfume solvents are well known in the art, and the conventional ones can be used herein, e.g., dipropylene glycol, diethylene glycol, $C_1$–$C_6$ alcohols, etc.

Other Cosmetically Active Ingredients

In addition to or in place of perfume, the compositions hereof can also comprise other cosmetically active ingredients or medicaments. Cosmetically active ingredients are compounds or materials which directly affect the appearance, feel, smell, or comfort of the skin, or which protect the skin from environmental factors (e.g., sun light). Medicaments are compounds or materials that have a direct medicinal or neurological effect (excluding $C_1$–$C_6$ alcohols). Such materials are well known and recognized in the art.

Cosmetically active ingredients include, but are not limited to, perfumes (as described above), skin conditioners such as skin moisturizers, humectants, and emollients, sunscreens, and pigments intended to color skin or aid in tanning of the skin. Medicaments include, but are not limited to, anti-acne ingredients, antibiotics, antimicrobials, antifungals, antivirals, antibacterials, antiprotozols, anti-inflammatory actives, astringents, antiseptics, etc. Various preferred cosmetically active ingredients and medicaments are described in detail below.

Skin Conditioners

The compositions can contain one or more skin conditioners. These materials are typically used at a level of from about 0.1% to about 20%, more preferably from about 1% to about 10% and most preferably from about 2% to about 5%. Skin conditioners include, but are not limited to, moisturizers, humectants, and emollients. Exemplary moisturizers and emollients include urea; guanidine; glycolic acid and glycolate salts (e.g., ammonium and quaternary alkyl ammonium); lactic acid and lactate salts (e.g., ammonium and quaternary alkyl ammonium); aloe vera in any of its variety of forms (e.g., aloe vera gel); polyhydroxy alcohols such as sorbitol, glycerol, hexanetriol, propylene glycol, hexylene glycol and the like; polyethylene glycol; sugars and starches; sugar and starch derivatives (e.g., alkoxylated glucose); hyaluronic acid; lactamide monoethanolamine; acetamide monoethanolamine; and mixtures thereof.

Examples of suitable emollients include, but are not limited to, volatile and non-volatile silicone oils, highly branched hydrocarbons, and non-polar carboxylic acid and alcohol esters, and mixtures thereof. Emollients useful in the instant invention are further described in U.S. Pat. No. 4,919,934, Deckner et al., issued Apr. 24, 1990, which is incorporated herein by reference in its entirety.

The emollients, in particular, when used typically comprise in total from about 0.05% to about 50%, preferably from about 0.5% to about 25%, and more preferably from about 1% to about 10% by weight of the compositions useful in the present invention.

Preferred emollients are nonvolatile, insoluble silicone conditioning agents. The nonvolatile, insoluble silicone fluid will preferably have average viscosity of at least about 1,000, preferably from about 1,000 to about 2,000,000, centistokes at 25° C., more preferably from about 10,000 to about 1,800,000 centistokes, even more preferably from about 100,000 to about 1,500,000 centistokes. Lower viscosity nonvolatile silicone conditioning agents, however, can also be used, as can volatile silicones, and water soluble silicones.

Suitable nonvolatile silicone fluids for use in hair conditioning agents include polyalkyl siloxanes, polyaryl siloxanes, polyalkylaryl siloxanes, polyether siloxane copolymer and mixtures thereof. However, other silicone fluids having hair conditioning properties may be used. The nonvolatile polyalkyl siloxane fluids that may be used include, for example, polydimethylsiloxanes. These siloxanes are available, for example, from the General Electric Company as a Viscasil series and from Dow Corning as the Dow Corning 200 series. Preferably, the viscosity ranges from about 10 centistokes to about 100,000 centistokes at 25° C.

The polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid.

The polyether siloxane copolymer that may be used includes, for example, a polypropylene oxide modified dimethylpolysiloxane (e.g., Dow Corning DC-1248) although ethylene oxide or mixtures of ethylene oxide and propylene oxide may also be used. The ethylene oxide and polypropylene oxide level must be sufficiently low to prevent solubility in water and the composition hereof.

Silicone fluids hereof also include polyalkyl or polyaryl siloxanes with the following structure:

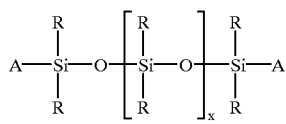

wherein R is alkyl or aryl, and x is an integer from about 7 to about 8,000 may be used. "A" represents groups which block the ends of the silicone chains.

The alkyl or aryl groups substituted on the siloxane chain (R) or at the ends of the siloxane chains (A) may have any structure as long as the resulting silicones remain fluid at room temperature, are hydrophobic, are neither irritating, toxic nor otherwise harmful when applied to the skin, are compatible with the other components of the composition, are chemically stable under normal use and storage conditions, and are capable of being deposited on and of conditioning skin.

Suitable A groups include methyl, methoxy, ethoxy, propoxy, and aryloxy. The two R groups on the silicone atom may represent the same group or different groups. Preferably, the two R groups represent the same group. Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred.

References disclosing suitable silicone fluids include U.S. Pat. No. 2,826,551, Geen; U.S. Pat. No. 3,964,500, Drakoff, issued Jun. 22, 1976; U.S. Pat. No. 4,364,837, Pader; and British Patent 849,433, Woolston. All of these patents are incorporated herein by reference. Also incorporated herein by reference is Silicon Compounds distributed by Petrarch Systems, Inc., 1984. This reference provides an extensive (though not exclusive) listing of suitable silicone fluids.

Another specific silicone fluid material that can be especially useful in the silicone conditioning agents is insoluble silicone gum. The term "silicone gum", as used herein, means polyorganosiloxane materials having a viscosity at 25° C. of greater than or equal to 1,000,000 centistokes. Silicone gums are described by Petrarch and others including U.S. Pat. No. 4,152,416, Spitzer et al., issued May 1, 1979, and Noll, Walter, *Chemistry and Technology of Silicones*, New York: Academic Press 1968. Also describing silicone gums are General Electric Silicone Rubber Product Data Sheets SE 30, SE 33, SE 54 and SE 76. All of these described references are incorporated herein by reference. The "silicone gums" will typically have a mass molecular weight in excess of about 200,000, generally between about 200,000 and about 1,000,000. Specific examples include polydimethylsiloxane, (polydimethylsiloxane) (methylvinylsiloxane) copolymer, poly(dimethylsiloxane) (diphenyl siloxane)(methylvinylsiloxane) copolymer and mixtures thereof.

Other skin conditioners include oily materials, such as hydrocarbon oils and long chain esters. Suitable esters hereof include those having at least 10 carbon atoms, e.g., fatty esters, and include esters with hydrocarbyl chains derived from fatty acids or alcohols, e.g., mono-esters, polyhydric alcohol esters, and di- and tri-carboxylic acid esters. The hydrocarbyl radicals of the fatty esters hereof can also include or have covalently bonded thereto other compatible functionalities, such as amides and alkoxy moieties (e.g., ethoxy or ether linkages, etc.).

Hydrocarbon oils include cyclic hydrocarbons, straight chain aliphatic hydrocarbons (saturated or unsaturated), and branched chain aliphatic hydrocarbons (saturated or unsaturated). Straight chain hydrocarbon oils will preferably contain from about 12 to about 19 carbon atoms. Branched chain hydrocarbon oils can and typically may contain higher numbers of carbon atoms. Specific examples include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used. Exemplary branched-chain isomers are highly branched saturated or unsaturated alkanes, such as the permethyl-substituted isomers, e.g., the permethyl-substituted isomers of hexadecane and eicosane, such as 2, 2, 4, 4, 6, 6, 8, 8-dimethyl-10-methylundecane and 2, 2, 4, 4, 6, 6-dimethyl-8-methylnonane, sold by Permethyl Corporation.

Monocarboxylic acid esters hereof inlude esters of alcohols and/or acids of the formula R' COOR wherein alkyl or alkenyl radicals and the sum of carbon atoms in R' and R is at least 10, preferably at least 20.

Fatty esters include, for example, alkyl and alkenyl esters of fatty acids having aliphatic chains with from about 10 to about 22 carbon atoms, and alkyl and alkenyl fatty alcohol carboxylic acid esters having an alkyl and/or alkenyl alcohol-derived aliphatic chain with about 10 to about 22 carbon atoms, and combinations thereof.

The mono-carboxylic acid ester need not necessarily contain at least one chain with at least 10 carbon atoms, so long as the total number of aliphatic chain carbon atoms is at least 10. Examples include diisopropyl adipate, diisohexyl adipate, and diisopropyl sebacate.

Di- and tri-alkyl and alkenyl esters of carboxylic acids can also be used. These include, for example, esters of $C_4$–$C_8$ dicarboxylic acids such as $C_1$–$C_{22}$ esters (preferably $C_1$–$C_6$) of succinic acid, glutaric acid, adipic acid, hexanoic acid, heptanoic acid, and octanoic acid.

Polyhydric alcohol esters include alkylene glycol esters, for example ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Glycerides include mono-, di-, and tri-glycerides. More specifically, included are the mono-, di-, and trimesters of glycerol and long chain carboxylic acids, such as $C_{10}$–$C_{22}$ carboxylic acids. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include triolein and tristearin glyceryl dilaurate.

Sunscreens

The compositions useful in the methods of the present invention can also optionally comprise at least one sunscreening agent. A wide variety of one or more sunscreening agents are suitable for use in the present invention and are described in U.S. Pat. No. 5,087,445, Haffey et al., issued Feb. 11, 1992; U.S. Pat. No. 5,073,372, to Turner et al., issued Dec. 17, 1991; U.S. Pat. No. 5,073,371, Turner et al., issued Dec. 17, 1991; and Segarin, et al., at Chapter VIII, pages 189 et seq., of *Cosmetics Science and Technology*, all of which are incorporated herein by reference in their entirety.

Preferred among those sunscreens which are useful in the compositions of the instant invention are those selected from the group consisting of ethylhexyl p-methoxycinnamate, octocrylene, octyl salicylate, oxybenzone, and mixtures thereof.

Other useful sunscreens include the solid physical sunblocks such as titanium dioxide (e.g., micronized titanium dioxide, 0.03 microns), zinc oxide, silica, iron oxide and the like.

Still other useful sunscreens are those disclosed in U.S. Pat. No. 4,937,370, Sabatelli, issued Jun. 26, 1990 and U.S. Pat. No. 4,999,186, Sabatelli et al., issued Mar. 12, 1991; these two references are incorporated by reference herein in their entirety.

Generally, the sunscreens can comprise from about 0.5% to about 20% of the compositions useful herein. Exact amounts will vary depending upon the sunscreen chosen and the desired Sun Protection Factor (SPF). SPF is a commonly used measure of photoprotection of a sunscreen against erythema. See *Federal Register*, Vol. 43, No. 166, pp 38206–38269, Aug. 25, 1978, which is incorporated herein by reference in its entirety.

Surfactants

Surfactants can be used as cosmetically active ingredients for cleaning purposes, or to boost foaming properties of the composition, e.g., anionic, amphoteric, and nonionic surfactants, or for skin conditioning, e.g., cationic surfactants. Anionic, amphoteric, zwitterionc and nonionic surfactants, which can also be useful as emulsifiers, are described further below.

Cationic surfactants include those that contain amino or quaternary ammonium hydrophilic moieties which are positively charged when dissolved in the aqueous composition of the present invention. Cationic surfactants among those useful herein are disclosed in the following documents, all incorporated by reference herein: M.C. Publishing Co., *McCutcheon's. Detergents & Emulsifiers*, (North American edition 1979); Schwartz, et al., *Surface Active Agents, Their Chemistry and Technology*, New York: Interscience Publishers, 1949; U.S. Pat. No. 3,155,591, Hilfer, issued Nov. 3, 1964; U.S. Pat. No. 3,929,678, Laughlin, et al., issued Dec. 30, 1975; U.S. Pat. No. 3,959,461, Bailey, et al., issued May 25, 1976; and U.S. Pat. No. 4,387,090, Bolich, Jr., issued Jun. 7, 1983. If included in the compositions of the present invention, the cationic surfactant is present at from about 0.05% to about 5%.

Among the quaternary ammonium-containing cationic surfactant materials useful herein are those of the general formula:

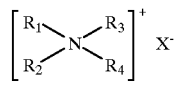

wherein $R_1$–$R_4$ are independently an aliphatic group of from about 1 to about 22 carbon atoms, or an aromatic, alkoxy, polyoxyalkylene, alkylamido, hydroxyalkyl, aryl or alkylaryl group having from about 12 to about 22 carbon atoms; and X is an anion selected from halogen, acetate, phosphate, nitrate and alkylsulfate radicals. The aliphatic groups may contain, in addition to carbon and hydrogen atoms, ether linkages, and other groups such as amino groups. The longer chain aliphatic groups, eg., those of about 12 carbons, or higher, can be saturated or unsaturated.

Other quaternary ammonium salts useful herein are diquaternary ammonium salts, such as tallow propane diammonium dichloride.

Quaternary ammonium salts include dialkyldimethylammonium chlorides, wherein the alkyl groups have from about 12 to about 22 carbon atoms and are derived from long-chain fatty acids, such as hydrogenated tallow fatty acid (tallow fatty acids yield quaternary compounds wherein $R_1$ and $R_2$ have predominately from 16 to 18 carbon atoms). Di-(saturated or unsaturated tallow) dimethyl ammonium salts are-particularly preferred.

Salts of primary, secondary and tertiary fatty amines are also suitable cationic surfactant materials. The alkyl groups of such amines preferably have from about 12 to about 22 carbon atoms, and may be substituted or unsubstituted. Such amines, useful herein, include stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (5 moles E.O.) stearylamine, dihydroxy ethyl stearylamine, and arachidylbehenylamine. Suitable amine salts include the halogen, acetate, phosphate, nitrate, citrate, lactate and alkyl sulfate salts. Such salts include stearylamine hydrochloride, soyamine chloride, stearylamine formate, N-tallowpropane diamine dichloride and stearamidopropyl dimethylamine citrate. Cationic amine surfactants included among those useful in the present invention are disclosed in U.S. Pat. No. 4,275,055, Nachtigal, et al., issued Jun. 23, 1981, incorporated by reference herein.

Cationic Polymer Conditioning Agent

The compositions of the present invention can also comprise a cationic organic polymer conditioning agent. The polymeric cationic conditioning agent hereof will generally be present at levels of from about 0.05% to about 5%, preferably from about 0.1% to about 4%, more preferably from about 0.2% to about 3%, by weight, of the composition. Preferably the cationic organic polymeris sufficiently soluble in water to form a substantially clear solution to the naked eye at a concentration of 0.1% in water (distilled or equivalent) at 25° C.

The cationic polymers hereof will generally have a weight average molecular weight which is at least about 5,000, typically at least about 10,000, and is less than about 10 million. Preferably, the molecular weight is from about 100,000 to about 2 million.

The cationic polymers typically will have cationic nitrogen-containing moieties such as quaternary ammonium or cationic amino moieties, or a mixture thereof. The precise cationic charge density is not believed to be critical to the invention. However, for practical reasons, the charge density should be of a level such that efficient substantivity between the polymer and the hair can be attained. Any anionic counterions can be utilized for the cationic polymers so long as the water solubility criteria is met. Suitable counterions include halides (e.g., Cl, Br, I, or F, preferably Cl, Br, or I), sulfate, and methylsulfate. Others can also be used, as this list is not exclusive. Generally, it is preferred that cationic charge density be at least about 0.2 meq/gram, more preferably at least about 0.4 meq/gram, at the pH of intended use.

The cationic nitrogen-containing moiety will be present generally as a substituent, on a fraction of the total monomer units of the cationic hair conditioning polymers. Thus, the cationic polymer can comprise copolymers, terpolymers, etc. of quaternary ammonium or cationic amine-substituted monomer units and other non-cationic units referred to herein as spacer monomer units. Such polymers are known in the art, and a variety can be found in the *CTFA Cosmetic Ingredient Dictionary*, 3rd edition, edited by Estrin, Crosley, and Haynes, (The Cosmetic, Toiletry, and Fragrance Association, Inc., Washington, D.C., 1982).

Suitable cationic polymers include, for example, copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. The alkyl and dialkyl substituted monomers preferably have $C_1$–$C_7$ alkyl groups, more preferably $C_1$–$C_3$ alkyl groups. Other suitable spacer monomers include vinyl esters, vinyl alcohol (made by hydrolysis of polyvinyl acetate), maleic anhydride, propylene glycol, and ethylene glycol.

The cationic amines can be primary, secondary, or tertiary amines, depending upon the particular species and the pH of the shampoo. In general, secondary and tertiary amines, especially tertiary amines, are preferred.

Suitable cationic amino and quaternary ammonium monomers include, for example, vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the $C_1$–$C_3$ alkyls, more preferably $C_1$ and $C_2$ alkyls.

Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably $C_1$–$C_7$ hydrocarbyls, more preferably $C_1$–$C_3$, alkyls.

The cationic polymers hereof can comprise mixtures of monomer units derived from amine- and/or quaternary ammonium-substituted monomer and/or compatible spacer monomers.

Suitable cationic conditioning polymers include, for example: copolymers of 1-vinyl-2-pyrrolidone and 1-vinyl-3-methyl-imidazolium salt (e.g., chloride salt) (referred to in the industry by the Cosmetic, Toiletry, and Fragrance Association, "CTFA", as Polyquaternium-16), such as those commercially available from BASF Wyandotte Corp. (Parsippany, N.J., USA) under the LUVIQUAT tradename (e.g., LUVIQUAT FC 370 and FC 905); copolymers of 1-vinyl-2-pyrrolidone and dimethylaminoethyl methacrylate (referred to in the industry by CTFA as Polyquaternium-11) such as those commercially available from Gaf Corporation (Wayne, N.J., USA) under the GAFQUAT tradename (e.g., GAFQUAT 755N); cationic diallyl quaternary ammonium-containing polymers, including, for example, dimethyldiallylammonium chloride homopolymer and copolymers of acrylamide and dimethyldiallylammonium chloride, referred to in the industry (CTFA) as Polyquaternium 6 and Polyquaternium 7, respectively, such materials being available from Merck and Co., Inc. in their Merquat® series; copolymers of acrylamide and dimethyl diallyl ammonium chloride, such as those available under the MERQUAT tradename from Calgon Corp. (Pittsburgh, Pa., USA) (e.g., MERQUAT 550); and mineral acid salts of amino-alkyl esters of homo- and co-polymers of unsaturated carboxylic acids having from 3 to 5 carbon atoms, as described in U.S. Pat. No. 4,009,256, incorporated herein by reference.

Other cationic polymers that can be used include polysaccharide polymers, such as cationic cellulose derivatives and cationic starch derivatives.

Cationic polysaccharide polymer materials suitable for use herein include those of the formula:

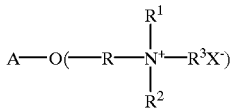

wherein:
A is an anhydroglucose residual group, such as a starch or cellulose anhydroglucose residual,
R is an alkylene oxyalkylene, polyoxyalkylene, or hydroxyalkylene group, or combination thereof, $R^1$, $R^2$, and $R^3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^1$, $R^2$ and $R^3$) preferably being about 20 or less, and X is an anionic counterion, as previously described.

The degree of cationic substitution is typically from about 0.01–1 cationic groups per anhydroglucose unit.

Cationic cellulose is available from Amerchol Corp. (Edison, N.J., USA) in their Polymer JR® and LR® series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted opoxide, referred to in the industry (CTFA) as Polyquaternium 24. These materials are available from Amerchol Corp. (Edison, N.J., USA) under the tradename Polymer LM-200.

Other cationic polymers that can be used include cationic guar gum derivatives, such as guar hydroxypropyltrimonium chloride (commercially available from Celanese Corp. in their Jaguar® series). Other materials include quaternary nitrogen-containing cellulose ethers (e.g., as described in U.S. Pat. No. 3,962,418, incorporated by reference herein), and copolymers of etherified cellulose and starch (e.g., as described in U.S. Pat. No. 3,958,581, incorporated by reference herein).

Other cosmetic actives include, but are not limited to: skin penetration aids such as DMSO, 1-dodecyl-azacycloheptan-2-one (available as Azone from the Upjohn Co.) and the like; artificial tanning agents such as dihydroxyacetone and the like; skin bleaching (or lightening) agents including but not limited to hydroquinone, ascorbic acid, kojic acid and sodium metabisulfite; antioxidants; and agents which sooth skin or aid in healing of irritated skin, nonlimiting examples of these aesthetic components include panthenol, Clove oil, camphor, eucalyptus oil, eugenol, menthyl lactate, witch hazel distillte, allantoin, bisabalol, and the like.

Medicaments

Medicaments that can be added include anti-acne ingredients such as salicylic acid, pantothenic acid and pantothenic acid derivatives (e.g., alcohol, aldehyde, alcohol ester, acid ester derivatives, etc., especially alcohol derivatives such as panthenol. A safe and effective amount of the medicament is included in the compositions to achieve the intended medical effect at the expected unit dosage. The medicaments are typically used at levels of about 0.1% to about 10% by weight of the composition.

Examples of other medicaments include keratolytics such as sulfur, lactic acid, glycolic, pyruvic acid, urea, resorcinol, and N-acetylcysteine; retinoids such as retinoic acid and its derivatives (e.g., cis and trans); antibiotics, antimicrobials, antibacterials, antifungals, antiprotozoals, and antivirals (e.g., benzoyl peroxide, octopirox, erythromycin, tetracyclin, triclosan, azelaic acid and its derivatives, phenoxy ethanol and phenoxy proponol, ethylacetate, clindamycin and meclocycline, triclosan, chlorhexidine, tetracycline, neomycin, miconazole hydrochloride, octopirox, parachlorometaxylenol, nystatin, tolnaftate, clotrimazole, and the like); sebostats such as flavinoids; hydroxy acids; antipruritic drugs including, for example, pharmaceutically-acceptable salts of methdilizine and trimeprazine; and bile salts such as scymnol sulfate and its derivatives, deoxychloate, and cholate.

Also, useful are non-steroidal anti-inflammatory drugs (NSAIDS). The NSAIDS can be selected from the following categories: propionic acid derivatives; acetic acid derivatives; fenamic acid derivatives; biphenylcarboxylic acid derivatives; and oxicams. All of these NSAIDS are fully described in the U.S. Pat. No. 4,985,459 to Sunshine et al., issued Jan. 15, 1991, incorporated by reference herein. Most preferred are the propionic NSAIDS including but not limited to aspirin, acetaminophen, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofin, tiaprofenic acid, fluprofen and bucloxic acid. Also useful are the steroidal anti-inflammatory drugs including hydrocortisone and the like.

Coolant Compositions

The compositions hereof can be used for a wide range of topical skin care compositions. They can be in the form of liquids, creams, lotions, and gels. Specific examples include toiletries such as after-shave lotions (i.e., post-shave lotions), pre-shave lotions, shaving aids such as shaving creams, gels and lotions, deodorants, perfumes, colognes, liquid soap or detergents, face creams, hand creams, skin creams, sunburn lotions, and sunscreen lotions. Medicament products include first aid and antiseptic products, anti-acne ointments, and topical anti-inflammatory compositions.

The aqueous vehicle can contain ingredients to modify the physical properties of the composition, such as thickeners, gelling agents, and viscosity modifiers. The compositions can also contain other ingredients, such as pigments, preservatives, pH modifiers, etc. In general, it is preferred for pH of the compositions to be between about pH 5.5 and about pH 8.5 in order to minimize burning or irritation of the skin although it is not intended to necessarily limit this invention to such range. Certain products, such as astringents containing acidic agents, may need to be outside this range for optional effectiveness. However, such products are still intended to be encompassed herein since long lasting cooling with relatively low skin burning and irritation can still be obtained.

The essential coolants hereof are insoluble in water. It is therefore preferred to incorporate them into the compositions in a way so that they remain stably distributed throughout the composition. This can be done by forming a dispersion, emulsion, or microemulsion, with the coolants solubilized in a suitable solvent that then forms the dispersion or emulsion (including microemulsions) in the aqueous carrier. Emulsion systems include oil-in-water, water-in-oil, water-in-oil-in-water, and oil-in-water-in-silicone emulsions. The emulsions can cover a broad range of consistencies including thin lotions (which can also be suitable for spray or aerosol delivery), creamy lotions, light creams, heavy creams, and the like. Suitable solvents for the coolants include lipophilic or nonpolar solvents such as diethylene glycol, dipropylene glycol, $C_1$–$C_6$ alcohols, acetone, and other organic solvents, many of which are also suitable for use as perfume solvents. Accordingly, the perfume and coolant components can be combined in a common solvent stage which is then incorporated into the composition.

Emulsion forming techniques are well known in the art. Suitable emulsifiers for use herein are anionic, nonionic, cationic, amphoteric, and zwitterionic surfactants. Surfactants can also be included herein, at suitable levels, as cosmetically active ingredients. Cationic surfactants, e.g., quaternary ammonium compounds, can be effective skin conditioners. Anionic, nonionic, amphoteric, and zwitterionic surfactants can be effective cleaning ingredients.

The compositions useful in the methods of the present invention can optionally comprise one or more surfactants. The surfactants can be present at a level from about 0.1% to about 20%, more preferably from about 0.2% to about 10%, and most preferably from about 1% to about 7.5%. Examples of a broad variety of surfactants useful herein are described in McCutcheon's, *Detergents and Emulsifiers*, North American Edition (1986), published by Allured Publishing Corporation, which is incorporated herein by reference in its entirety.

Suitable surfactants include, but are not limited to, nonionic surfactants such as polyalkylene glycol ethers of fatty alcohols. Suitable anionic surfactants include taurates, alkyl sulfates, alkyl ethoxylated sulfates, and alkyl phosphates and alkyl ethoxylated phosphates. Nonlimiting examples of these surfactants include isoceteth-20, sodium methyl cocoyl taurate, sodium methyl oleoyl taurate, and sodium lauryl sulfate. See U.S. Pat. No. 4,800,197, to Kowcz et al., issued Jan. 24, 1989, which is incorporated herein by reference in its entirety.

Suitable alkyl and alkyl ethoxylated phosphates are of the formulas $ROPO_4M$ and $RO(C_2H_4O)_xPO_4M$ wherein R is alkyl or alkenyl of from about 8–24 carbon atoms, x is 1 to 10, and M is a water soluble cation such as ammonium, or alkali or alkaline earth metal such as sodium, potassium, and magnesium, or an amine such as triethanolamine. These are also referred to as phosphate esters.

Suitable alkyl and alkyl ethoxylated sulfates are of the formulas $ROSO_3M$ and $RO(C_2H_4O)_xSO_3M$ wherein R is alkyl or alkenyl of from about 8–24 carbon atoms, x is 1 to 10, and M is a water soluble cation such as ammonium, or alkali or alkaline earth metal such as sodium, potassium, and magnesium, or an amine such as triethanolamine.

Other anionic surfactants include succinamates, e.g., disodium N-octadecylsulfosuccinamate, tetrasodium N-(1,2-dicarboxy-ethyl)-N-octadecylsulfosuccinamate, and dioctyl, dihexyl, and diamyl esters of sodium sulfosuccinic acid.

Suitable nonionic surfactants include: polyethylene oxide condensates of alkyl phenols, e.g., the condensation products of $C_6$–$C_{20}$ alkyl phenols with ethylene oxide, with a molar ratio of from about 10 to about 60 moles, ethylene oxide per mole of alkyl phenol; condensation products of ethylene oxide with the reaction product of propylene oxide and ethylene diamine, e.g., compounds with about 40%–80% polyoxyethylene by weight having a molecular weight of from about 5,000–11,000, wherein the ethylene diamine/propylene oxide portion has a molecular weight of about 2,500–3,000; condensation products of $C_8$–$C_{18}$ aliphatic alcohols (straight or branched chain) with ethylene oxide, with, for example about 10–30 moles of ethylene oxide per mole of alcohol; polysorbates; alkylpolyglycosides; polyethylene glycol glyceryl fatty esters; etc.

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula

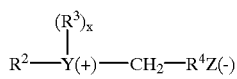

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of amphoteric surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-higher alkyl aspartic acids such as those produced according to the teaching of U.S. Pat. No. 2,438, 091, and the products sold under the trade name "Miranol" and described in U.S. Pat. No. 2,528,378.

Other amphoteric surfactants also include sultaines and amidosultaines. Sultaines, including amidosultaines, include for example, cocodimethylpropylsultaine, stearyldimethylpropylsultaine, lauryl-bis-(2-hydroxyethyl) propylsultaine and the like; and the amidosultaines such as cocoamidodimethylpropylsultaine, stearylamidododimethylpropylsultaine, laurylamidobis-(2-hydroxy-ethyl) propylsultaine, and the like. Preferred are amidohydroxysultaines such as the $C_{12}$–$C_8$ hydrocarbyl amidopropyl hydroxysultaines, especially $C_{12}$–$C_4$ hydrocarbyl amido propyl hydroxy-sultaines, e.g., laurylamidopropyl hydroxysultaine and cocamidopropyl hydroxysultaine. Other sultaines are disclosed in U.S. Pat. No. 3,950,417, issued Apr. 13, 1976, incorporated herein by reference.

Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gammacarboxypropyl betaine, and lauryl bis-(2-hydroxypropyl)alphacarboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the $RCONH(CH_2)_3$ radical is attached to the nitrogen atom of the betaine are also useful in this invention. Preferred betaines for use in the present compositions are cocoamidopropyl betaine, cocobetaine, lauryl amidopropyl betaine, and oleyl betaine.

Other specific amphoterics include imidazolinium materials depicted by formula:

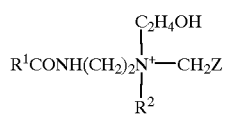

(I)

wherein $R^1$ is $C_8$–$C_{22}$ alkyl or alkenyl, $R^2$ is hydrogen, $CO_2M$, $CH_2CO_2M$, or $CH_2CH_2M$, Z is $CO_2M$ or $CH_2CO_2M$, and M is hydrogen, alkali metal, alkaline earth metal, ammonium or alkanol ammonium.

Materials included are cocoamphocarboxypropionate, cocoamphocarboxy propionic acid, and cocoamphocarboxyglycinate. Mixtures of these materials may also be used. The most preferred material of this type for use in the present invention is cocoamphocarboxyglycinate (also known as cocoamphodiacetate).

Another specific class of amphoteric surfactants is defined by the aminoalkanoates of formula:

and the iminodialkanoates of formula:

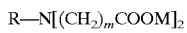

and mixtures thereof; wherein n and m are numbers from 1 to 4, R is $C_8$–$C_{22}$ alkyl or alkenyl, and M is hydrogen, alkali metal, alkaline earth metal, ammonium or alkanolammonium.

Examples of such amphoteric surfactants include n-alkylamino-propionates, n-alkyliminodipropionates, and mixtures thereof.

Gelling Agents and Thickeners

Optional components of the compositions useful in the instant invention also include gelling agents and thickeners. A preferred gelling agent is a carboxylic copolymer (acrylic acid copolymer), for example Carbomer 954 and Carbomer 1342 (available as Carbopol 954 and Carbopol 1342 from B.F. Goodrich). These polymers are more fully described in U.S. Pat. No. 4,509,949, to Huang et al., issued Apr. 5, 1985, and U.S. Pat. No. 2,798,053, to Brown, issued Jul. 2, 1957, both of which are incorporated herein by reference in their entirety. Also useful are the acrylate/alkyl acrylate crosspolymers such as Acrylates/C10–C30 Alkyl Acrylate Crosspolymer (available as Pemulen TR-1 and Pemulen TR-2 from Goodrich).

These polymers can be used at levels from about 0.015% to about 0.75%, preferably from about 0.05% to about 0.25% and most preferably from about 0.075% to about 0.175% in the compositions herein.

Other gellants and thickeners include alkyl glycols, alkyl modified cellulose polymers, gums such as guar gums and xanthan gums, and mixtures thereof. Exemplary alkyl modified cellulose polymers, specifically those selected from the group consisting of methylcellulose, ethylcellulose, hydroxybutyl methylcellulose, hydroxy ethylcellulose, hydroxy propylcellulose, hydroxypropyl methylcellulose cellulose, and mixtures theroef.

Suitable thickening systems are also disclosed in U.S. Pat. No. 5,106,609, Bolich et al., issued Apr. 21, 1992, U.S. Pat. No. 5,104,646, Bolich et al., issued Apr. 14, 1992, U.S. Pat. No. 5,100,658, Bolich et al., issued Mar. 31, 1992, and U.S. Pat. No. 5,100,657, Ansher-Jackson et al., issued Mar. 31, 1992, all of which are incorporated herein by reference. These patents disclose thickened vehicle systems containing water, a surfactant or water insoluble polymer, and a nonionic, hydrophobically modified water soluble polymer, such as a nonionic, long chain alkylated (e.g., hydroxyalkyl, urethane, or acyl radicals) cellulosic polymer, e.g., Natrosol Plus CS Grade 67, a hydrophobically modified (cetylated) hydroxyethyl cellulose available from Aqualon Corporation, Wilmington,. Del., USA. Such compositions typically comprise from about 0.1% to about 10% of the polymer, from 0.02% to about 10.0% of a surfactant (preferably a water insoluble surfactant, and also preferably no more than about 2% water soluble surfactant) or from about 0.3% to about 5% of a water soluble polymeric thickener (e.g., locust bean and guar gums), and water.

Other aqueous vehicle systems are gels based upon water, a lipid or lipid-type ingredient (e.g., fatty alcohol), and a cationic surfactant.

Suspending agents also include long chain acyl derivative materials, long chain amine oxides, or mixtures of such materials. Preferably such suspending agents are present in the composition in crystalline form. Suspending agents of this type are described in U.S. Pat. No. 4,741,855, Grote and Russell, issued May 3, 1988, incorporated herein by reference. Included are ethylene glycol esters of fatty acids preferably having from about 16 to about 22 carbon atoms. More preferred are the ethylene glycol stearates, both mono and distearate, but particularly the distearate. Other suspending agents found useful are alkanol amides of fatty acids, preferably having from about 16 to about 22 carbon atoms, more preferably about 16 to 18 carbon atoms. Other long chain acyl derivatives include long chain esters of long chain fatty acids (e.g., stearyl stearate, cetyl palmitate, etc.); glyceryl esters (e.g., glyceryl distearate) and long chain esters of long chain alkanol amides (e.g., stearamide diethanolamide distearate, stearamide monoethanolamide stearate). Long chain acyl derivatives also include N,N-dihydrocarbyl amido benzoic acid and soluble salts thereof (e.g., Na and K salts), particularly N,N-di(hydrogenated) $C_{16}$, $C_{18}$ and tallow amido benzoic acid species of this family, which are commercially available from Stepan Company (Northfield, Ill., USA). Long chain acyl derivatives, ethylene glycol esters of long chain carboxylic acids, long chain amine oxides, and alkanol amides of long chain carboxylic acids in addition to the preferred materials listed above may be used as suspending agents. For example, it is contemplated that suspending agents with long chain hydrocarbyls having $C_8$–$C_{22}$ chains may be used.

Suspending agents also include long chain amine oxides such as alkyl ($C_{16}$–$C_{22}$) dimethyl amine oxides, e.g., stearyl dimethyl amine oxide.

The acyl derivative and amine oxide suspending agents are typically present in pourable, liquid formulations at a level of from about 0.1% to about 5.0%, preferably from about 0.5% to about 3.0%.

Another type of suspending agent that can be used is xanthan gum. Shampoo compositions utilizing xanthan gum as a suspending agent for the silicone hair conditioning component are described in U.S. Pat. No. 4,788,006, Bolich and Williams, issued Nov. 29, 1988, incorporated herein by reference. Xanthan gum is biosynthetic gum material that is commercially available. It is a heteropolysaccharide with a molecular weight of greater than 1 million. It is believed to contain D-glucose, D-mannose and D-glucuronate in the molar ratio of 2.8:2.0:2.0. The polysaccharide is partially acetylated with 4.7% acetyl. This information and other is found in Whistler, Roy L. Editor *Industrial Gums— Polysaccharides and Their Derivatives* New York: Academic Press, 1973. Kelco, a Division of Merck & Co., Inc. offers xanthan gum as Keltrol®. The gum, when used as the silicone hair conditioning component suspending agent, will typically be present in pourable, liquid formulations at a level of from about 0.3% to about 3%, preferably from about 0.4% to about 1.2% in the compositions of the present invention.

Combinations of long chain acyl derivatives and xanthan gum are disclosed as a suspending agent for silicone hair conditioners in U.S. Pat. No. 4,704,272, Oh et al., issued Nov. 3, 1987, incorporated herein by reference, and may also be used in the present compositions.

Another type of suspending agent that can be used is carboxyvinyl polymer. Preferred polymers are copolymers of acrylic acid crosslinked with polyallylsucrose as described in U.S. Pat. No. 2,798,053, Brown, issued Jul. 2, 1957, incorporated herein by reference. These polymers are provided by B.F. Goodrich Company as, for example, Carbopol 934, 940, 941, and 956.

A carboxyvinyl polymer is an interpolymer of a monomeric mixture comprising a monomeric olefinically unsaturated carboxylic acid, and from about 0.1% to about 10% by weight of the total monomers of a polyether of a polyhydric alcohol, which polyhydric alcohol contains at least four carbon atoms to which are attached at least three hydroxyl groups, the polyether containing more than one alkenyl group per molecule. Other monoolefinic monomeric materials may be present in the monomeric mixture if desired, even in predominant proportion.

Preferred polyhydric alcohols used to product carboxyvinyl polymers include polyols selected from the class consisting of oligosaccharides, reduced derivatives thereof in which the carbonyl group is converted to an alcohol group, and pentaerythritol; more preferred are oligosaccharides, most preferred is sucrose. It is preferred that the hydroxyl groups of the polyol which are modified be etherified with allyl groups, the polyol having at least two allyl ether groups per polyol molecule. When the polyol is sucrose, it is preferred that the sucrose have at least about five allyl ether groups per sucrose molecule. It is preferred that the polyether of the polyol comprise from about 0.1% to about 4% of the total monomers, more preferably from about 0.2% to about 2.5%.

Preferred monomeric olefinically unsaturated carboxylic acids for use in producing carboxyvinyl polymers used herein include monomeric, polymerizable, alpha-beta monoolefinically unsaturated lower aliphatic carboxylic acids; more preferred are monomeric monoolefinic acrylic acids of the structure

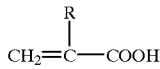

where R is a substituent selected from the group consisting of hydrogen and lower alkyl groups; most preferred is acrylic acid.

Preferred carboxyvinyl polymers used in formulations of the present invention have a molecular weight of at least about 750,000; more preferred are carboxyvinyl polymers having a molecular weight of at least about 1,250,000; most preferred are carboxyvinyl polymers having a molecular weight of at least about 3,000,000.

Materials that can also be used as suspension or gelling agents, include water soluble or colloidally water soluble polymers like cellulose ethers (e.g., hydroxyethyl cellulose), guar gum, polyvinyl alcohol, polyvinyl pyrrolidone, hydroxypropyl guar gum, starch and starch derivatives. In general, these are used at a level of from about 0.1% to about 10%, most commonly from about 0.3% to about 5.0% by weight of the composition.

Other Optional Components

A variety of additional ingredients can be incorporated into the compositions useful in the methods of the present invention. Non-limiting examples of these additional ingredients include polymers for aiding the film-forming properties and substantivity of the composition (such as a copolymer of eicosene and vinyl pyrrolidone, an example of which is available from GAF Chemical Corporation as Ganex V-220®); preservatives; colors and dyes; and sequestrants and chelators.

The compositions hereof can be dispensed from conventional containers or bottles, aerosol or nonaerosol spray containers, tubes, etc. Additionally, the compositions herein can be incorporated into a pad, which is used by rubbing or wiping against the skin. Preferably these pads comprise from about 50% to about 75% by weight of one or more layers of nonwoven fabric material and from about 20% to about 75% by weight (on dry solids basis) of a water soluble polymeric resin. Such pads are described in detail in U.S. Pat. No. 4,891,228, to Thaman et al., issued Jan. 2, 1990 and U.S. Pat. No. 4,891,227, to Thaman et al., issued Jan. 2, 1990; both of which are incorporated by reference herein.

The present invention further encompasses a method for providing a cooling sensation to the skin comprising applying an effective amount of any of the compositions hereof to the skin. The composition is left on the skin to provide an effective, long-lasting cooling sensation. Typically, from about 0.05 g to about 10 g per $cm^2$ of skin is applied.

EXAMPLES

The following examples serve to further describe and demonstrate embodiments within the scope of the invention, but are not to be construed as limitations of the present invention as many variations are possible without departing from the spirit of the invention. The scope of the invention is defined in the claims which follow.

Examples 1–5

Given below are examples of after shave lotions of the present invention.

|  | Examples | | | | |
|---|---|---|---|---|---|
| Ingredients (wt. %) | 1 | 2 | 3 | 4 | 5 |
| Ethanol | 20.00 | 0.00 | 10.00 | 30.00 | 5.00 |
| Perfume Component | 3.00 | 1.50 | 2.00 | 5.00 | 1.00 |
| Phosphate Ester [1] | 7.50 | 6.00 | 5.00 | 7.50 | 2.00 |
| Sorbitan Monooleate | 5.00 | 2.00 | 2.50 | 4.00 | 1.00 |
| Glydant Plus [2] | 0.15 | 0.20 | 0.18 | 0.10 | 0.18 |
| Disodium EDTA [3] | 0.10 | 0.10 | 0.10 | 0.10 | 0.10 |
| Butylene Glycol | 5.00 | 1.00 | 3.00 | 5.00 | 1.00 |
| Coolant 1 [4] | 0.08 | 0.16 | 0.14 | 0.12 | 0.06 |
| Coolant 2 [5] | 0.08 | 0.08 | 0.06 | 0.04 | 0.12 |
| Water | q.s. to 100% | | | | |

[1] Potassium Butylcarbatol Phosphate
[2] DMDM hydantoin and iodopropynyl butylcarbamate, available from Lonza, Inc. (Fairlawn, NJ, USA)
[3] Disodium ethylenediaminetetraacetate
[4] N,2,3-trimethyl-2-isopropylbutanamide
[5] N-ethyl p-menthan-3-carboxamide The above compositions are made by mixing Coolants 1 and 2, the perfume component, and phosphate ester surfactant to form a solution. A second solution is formed by mixing the disodium EDTA, Glydant Plus, butylene glycol, ethanol, and water. The first and second mixtures are then combined and mixed to form the final product.

The compositions can provide an effective, long-lasting cooling sensation to the skin with low or zero noticeable stinging to the skin, including cut or irritated skin.

Examples 6–10

Given below are examples of astringent cleaning compositions of the present invention.

|  | Examples | | | | |
|---|---|---|---|---|---|
| Ingredients (wt. %) | 6 | 7 | 8 | 9 | 10 |
| Ethanol | 30.00 | 30.00 | 20.00 | 30.00 | 20.00 |
| Salicylic Acid | 0.35 | 0.40 | 0.30 | 0.50 | 0.35 |
| Perfume Component | 0.10 | 0.10 | 0.05 | 0.08 | 0.15 |
| PEG (40) Hydrogenated Castor Oil [1] | 0.03 | 0.05 | 0.15 | 0.10 | 0.20 |
| Coolant 1 [2] | 0.08 | 0.12 | 0.12 | 0.05 | 0.12 |
| Coolant 2 [3] | 0.04 | 0.04 | 0.08 | 0.05 | 0.12 |
| Coolant 3 [4] (Optional) | 0.12 | 0.08 | 0.12 | 0.25 | 0.12 |
| Water | q.s to 100% | | | | |

[1] Polyethylene (40) glycol hydrogenated castor oil
[2] N,1,3-trimethyl-2-isopropylbutanamide
[3] N-ethyl p-menthan-3-carboxamide
[4] 1-Menthon-/d-iso-menthon glycerin ketal The perfume component, salicylic acid, ethanol, coolants, and surfactant are combined and mixed together to form a solution. This is then added to the water and mixed to form the final product. Optionally, Coolant 3 can be included in the compositions.

The compositions can provide an effective, long lasting cooling sensation to the skin, along with astringent benefits, with relatively low skin sting.

Example 11

Given below is a shave cream composition of the present invention.

| Ingredients | Example 11 |
|---|---|
| Stearic Acid | 6.30 |
| Lauramide DEA [1] | 1.00 |
| Triethanolamine | 3.90 |
| Perfume Component | 0.25 |
| Isobutane | 2.80 |
| Propane | 0.50 |
| Coolant 1 | 0.16 |
| Coolant 2 | 0.12 |
| Water | q.s. to 100% |

[1] Lauric diethanolamide

The shave cream is prepared by mixing and heating the water, stearic acid, lauramide DEA, and triethanolamine to about 75° C. to form a solution. The mixture is cooled to room temperature. The perfume component and sensates are then mixed together and added to the cooled mixture. This mixture is then dispensed in a conventional shave cream aerosol container along with the isobutane and propane propellants. Coolants 1 and 2 are as defined above. Optionally, Coolant 3 (as defined above) can also be added, e.g., at a level of about 0.12%.

The composition hereof can provide excellent shaving performance upon application to the face and shaving, along with providing a long-lasting cooling sensation to the skin, with low skin sting.

Example 12

Given below is a shave gel composition of the present invention.

| Ingredients (wt. %) | Example 12 |
| --- | --- |
| Palmitic Acid | 7.20 |
| Triethanolamine | 5.30 |
| Stearic Acid | 2.40 |
| Isopentane | 2.00 |
| PEG-14M [1] | 0.25 |
| Isobutane | 0.35 |
| Perfume Component | 0.25 |
| Coolant 1 | 0.16 |
| Coolant 2 | 0.06 |
| Water | q.s. to 100% |

[1] Polyethylene glycol (20,000 d.p.)

The shave gel is prepared by mixing and heating the water, palmitic acid, stearic acid, triethanolamide, and PEG-14M to about 75° C. to form a solution. The mixture is cooled to room temperature. The perfume component and coolants are mixed together to form a solution, which is then added to and mixed with the first mixture. Coolants 1 and 2 are as previously defined. Optionally, 0.12% of Coolant 3 can also be included. The composition is dispensed in a conventional aerosol can for shave gel compositions along with propellant.

The composition hereof can provide excellent shaving performance upon application to the face and shaving, along with providing a long-lasting cooling sensation to the skin, with low skin sting.

Example 13

A skin lotion according to the present invention is exemplified below.

| Ingredients (wt. %) | Example 13 |
| --- | --- |
| Carbomer [1] | 0.40 |
| Ethanol | 10.00 |
| Glycerin | 3.00 |
| Perfume Component | 0.80 |
| Sodium Hydroxide | 0.15 |
| Coolant 1 | 0.18 |
| Coolant 2 | 0.07 |
| Water | q.s. to 100 % |

[1] Carbopol 954 and Pemulen TR 2 (5:3 weight ratio), both being homopolymers of acrylic acid crosslinked with an allyl ether of pentaerythritol or an allyl ether of sucrose, available from B. F. Goodrich Co. (Brecksville, OH, USA)

The lotion is made by first mixing the water, carbomer, and glycerin. Next, a second mixture of the perfume component, ethanol, and coolants is prepared. Coolants 1 and 2 are as previously defined. Optionally, 0.25% of Coolant 3 as previously defined, can be added. The two mixtures are mixed together and neutralized with the NaOH. The resulting compositions can provide excellent skin moisturizing along with a long lasting cooling sensation with low skin sting.

Example 14

A skin lotion according to the present invention is exemplified below.

| Ingredients (wt. %) | Example 14 |
| --- | --- |
| Carbomer [1] | 0.33 |
| Octyl Methoxycinnamate | 7.50 |
| Triethanolamine | 1.30 |
| Glycerin | 1.00 |
| Stearic Acid | 1.00 |
| Cetyl Alcohol | 1.00 |
| Cetyl Palmitate | 0.50 |
| DEA-Cetyl Phosphate [2] | 0.75 |
| Perfume Component | 0.25 |
| Coolant 1 | 0.18 |
| Coolant 2 | 0.07 |
| Water | q.s. to 100% |

[1] Carbomer, as in Example 13.
[2] Diethanolamide salt of cetyl Phosphate

The sunscreen composition is prepared by mixing the water, carbomer, and glycerin and heating the mixture to about 80° C. The octyl methoxycinnamate, fatty alcohols, and stearic acid are then separately mixed together and heated to about 80° C. The two mixtures are mixed together and cooled to room temperature. The coolants and perfume component are separately mixed and then added to the composition. Coolants 1 and 2 are as defined above. Optionally, 0.25% of Coolant 3, as defined above, can be included. Finally the triethanolamide is mixed into the composition.

The composition, upon application to the skin, can provide the skin with excellent protection from U.V. light while also providing a long-lasting cooling sensation without skin sting.

What is claimed is:

1. A coolant composition for topical application to the skin comprising:

(I) first coolant component which is an acyclic carboxamide coolant component of the formula:

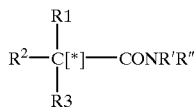

where:
(i) R' and R" independently are hydrogen, $C_1$–$C_5$ alkyl, or $C_1$–$C_8$ hydroxyalkyl, R' and R" provide a total of no more than 8 carbon atoms, and when R' is hydrogen, R" may also be alkyl carboxyalkyl of up to 6 carbon atoms
(ii) R' and R", when taken together, represent an alkylene group of up to 6 carbon atoms, the opposite ends of which are attached to the amide nitrogen atom to form a nitrogen hetero cycle, the carbon chain of which optionally being interrupted by oxygen;
(iii) $R^1$ is hydrogen or $C_1$–$C_5$ alkyl; $R^2$ and $R^3$ independently are $C_1$–$C_5$ alkyl; with the proviso that: (a) $R^1$, $R^2$, and $R^3$ together provide a total of at least 5 carbon atoms; and (b) when $R^1$ is hydrogen, $R^2$ is $C_2$–$C_5$ alkyl and $R^3$ is $C_3$–$C_5$ alkyl and at least one of $R^2$ and $R^3$ is branched;

(II) a second coolant component which is a 3-substituted-p-menthane of the formula:

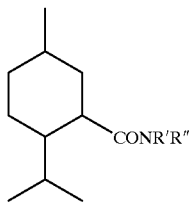

where
R', when taken separately, is hydrogen or an aliphatic radical containing up to 25 carbon atoms;
R", when taken separately, is hydroxy or an aliphatic radical containing up to 25 carbon atoms, with the proviso that when R' is hydrogen R" may also be an aryl radical of up to 10 carbon atoms selected from the group consisting of substituted phenyl, phenalkyl and substituted naphthyl, and pyridyl; and R' and R", when taken together with the nitrogen atom to which they are attached, represent a cyclic or heterocyclic group of from 1 to 25 carbon atoms;

(III) an aqueous vehicle; and (IV) a cosmetically active ingredient or medicament, or a mixture thereof;

wherein said composition contains no more than about 10% by weight of $C_1$–$C_6$ monohydric alcohol.

2. A coolant composition as in claim 1 wherein said composition comprises a perfume.

3. A coolant composition for topical application to the skin comprising:

(I) a first coolant component which is an acyclic carboxyamide coolant component of the formula:

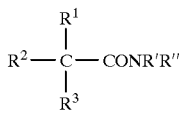

where:
(i) R' and R" independently are hydrogen, $C_1$–$C_5$ alkyl, or $C_1$–$C_8$ hydroxyalkyl, R' and R" provide a total of no more than 8 carbon atoms, and when R' is hydrogen, R" may also be alkyl-carboxyalkyl of up to 6 carbon atoms;

(ii) R' and R", when taken together, represent an alkylene group of up to 6 carbon atoms, the opposite ends of which are attached to the amide nitrogen atom to form a nitrogen hetero cycle, the carbon chain of which optionally being interrupted by oxygen;

(iii) $R^1$ is hydrogen or $C_1$–$C_5$ alkyl; $R^2$ and $R^3$ independently are $C_1$–$C_5$ alkyl; with the proviso that: (a) $R^1$, $R_2$, and $R^3$ together provide a total of at least 5 carbon atoms; and (b) when $R^1$ is hydrogen, $R^2$ is $C_2$–$C_5$ alkyl and $R^3$ is C–$C_5$ alkyl and at least one of $R^2$ and $R^3$ is branched;

(II) a second coolant component which is a 3-substituted-p-menthane of the formula:

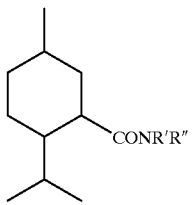

where
R', when taken separately, is hydrogen or an aliphatic radical containing up to 25 carbon atoms;
R", when taken separately, is hydroxy or an aliphatic radical containing up to 25 carbon atoms, with the proviso that when R' is hydrogen, R" may also be an aryl radical of up to 10 carbon atoms selected from the group consisting of substituted phenyl, phenalkyl, substituted naphthyl, and pyridyl; and R' and R", when taken together with the nitrogen atom to which they are attached, represent a cyclic or heterocyclic group of from 1 to 25 carbon atoms;

(III) an aqueous vehicle; and (IV) a cosmetically active ingredient or medicament, or a mixture thereof;

wherein said composition contains no more than about 30% by weight of $C_1$–$C_6$ monohydric alcohol, and wherein the weight ratio of component (I) to component (II) is from about 5:1 to about 1:5.

4. A coolant composition as in claim 3, wherein said weight ratio of component (I) to component (II) is from about 3:1 to about 1:3.

5. A coolant composition as in claim 4, wherein said weight ratio of component (I) to component (II) is from about 3:1 to about 1:1.

6. A coolant composition as in claim 1, wherein for said coolant component (I),
R' is hydrogen
R" is $C_1$–$C_5$ alkyl, $C_1$–$C_8$ hydroxyalkyl or alkylcarboxyalkyl of up to 6 carbon atoms;
$R^1$ is hydrogen or $C_1$–$C_5$ alkyl;
$R^2$ and $R^3$ independently are $C_1$–$C_5$ alkyl;
$R^1$, $R^2$, and $R^3$ together provide a total of at least 5 carbon atoms; and
when $R^1$ is hydrogen, $R^2$ is $C_2$–$C_5$ alkyl and $R^3$ is $C_3$–$C_5$ alkyl branched at the carbon atom in the alpha or beta position.

7. A coolant composition as in claim 6 wherein $R^1$, $R^2$ and $R^3$ are each $C_1$–$C_5$ alkyl.

8. A coolant composition as in claim 7, wherein $R^1$ is methyl, ethyl or n-propyl, and at least one of $R^2$ and $R^3$ has at least three carbon atoms and is branched at the alpha or beta carbon atom.

9. A coolant composition as in claim 8, wherein $R^1$, $R^2$ and $R^3$ provide a total of from 5–10 carbon atoms.

10. A coolant composition as in claim 9, wherein component (I) is N,2,3-trimethyl-2-isopropyl butanamide.

11. A coolant composition as in claim 1, wherein for said coolant component (II), R' and R" independently are hydrogen, $C_1$–$C_9$ straight or branched chain alkyl, $C_1$–$C_9$ straight or branched chain hydroxyalkyl or aminoalkyl or a $C_1$–$C_4$ acylated derivative thereof, or —$C_nH_{2n}COR'''$ or —$C_nH_{2n}COOR'''$ where —$C_nH_{2n}$ is a straight or branched chain alkylene group in which n is an integer of from 1–6 and R''' is hydrogen or $C_1$–$C_8$ alkyl.

12. A coolant composition as in claim 11, wherein said component (II) is N-ethyl-p-menthane-3-carboxamide.

13. A coolant composition as in claim 6, wherein for said coolant component (II), R' and R" independently are hydrogen, $C_1$–$C_9$ straight or branched chain alkyl, $C_1$–$C_9$ straight or branched chain hydroxyalkyl or aminoalkyl or a $C_1$–$C_4$ acylated derivative thereof, or —$C_nH_{2n}COR'''$ or —$C_nH_{2n}COOR'''$ where —$C_nH_{2n}$ is a straight or branched chain alkylene group in which n is an integer of from 1–6 and R''' is hydrogen or $C_1$–$C_8$ alkyl.

14. A coolant composition as in claim 13, further comprising a coolant of the formula:

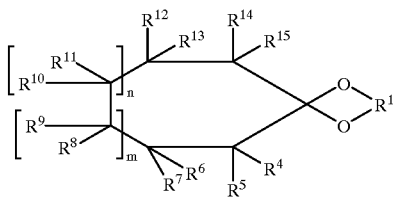

in which $R^4$ to $R^{15}$ independently of one another denote hydrogen or $C_1$–$C_6$ alkyl and m and n independently of one another denote zero or 1.

15. A coolant composition as in claim 1, which contains no more than about 5%, by weight, $C_1$–$C_6$ monohydric alcohol.

16. A coolant composition as in claim 1, comprising a cosmetically active ingredient selected from the group consisting of surfactants, conditioners, perfumes, and sunscreens.

17. A coolant composition as in claim 1, comprising a medicament selected from the group consisting of anti-acne and anti-inflammatory active ingredients.

18. A method of providing a cooling sensation to the skin comprising applying an effective amount, for providing a cooling sensation, of the composition of claim 1 to the skin.

19. A method of providing a cooling sensation to the skin comprising applying an effective amount, for providing a cooling sensation, of the composition of claim 2 to the skin.

20. A method of providing a cooling sensation to the skin comprising applying an effective amount, for providing a cooling sensation, of the composition of claim 16 to the skin.

21. A method of providing a cooling sensation to the skin comprising applying effective amount, for providing a cooling sensation, of the composition of claim 17 to the skin.

* * * * *